(12) United States Patent
Bercovici et al.

(10) Patent No.: US 10,564,158 B2
(45) Date of Patent: Feb. 18, 2020

(54) CHARACTERIZING KINETIC RESPONSES OF A LIGAND-FUNCTIONALIZED SURFACE

(71) Applicants: International Business Machines Corporation, Armonk, NY (US); Technion Research & Development Foundation Limited, Haifa (IL)

(72) Inventors: Moran Bercovici, Haifa (IL); Govind V. Kaigala, Pfaffikon (CH); Xander F. van Kooten, Zurich (CH); Nadya Ostromohov, Haifa (IL); Federico Paratore, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 155 days.

(21) Appl. No.: 15/627,512

(22) Filed: Jun. 20, 2017

(65) Prior Publication Data

US 2018/0364226 A1    Dec. 20, 2018

(51) Int. Cl.
*G01N 33/557* (2006.01)
*G01N 33/543* (2006.01)
(Continued)

(52) U.S. Cl.
CPC ............ *G01N 33/557* (2013.01); *B01L 3/021* (2013.01); *B01L 3/50273* (2013.01);
(Continued)

(58) Field of Classification Search
CPC ..... B01L 2200/0673; B01L 2300/0627; B01L 2300/0867; B01L 2300/161;
(Continued)

(56) References Cited

U.S. PATENT DOCUMENTS 6,143,574 A   11/2000  Karlsson et al.
9,175,421 B2  11/2015  Notcovich et al.
(Continued)

OTHER PUBLICATIONS

Munoz et al., "Real-Time Evaluation of Binding Mechanisms in Multivalent Interactions: A surface Plasmon Resonance Kinetic Approach", J. Am. Chem, 2013, 135 (16), abstract.
(Continued)

*Primary Examiner* — Betty J Forman
(74) *Attorney, Agent, or Firm* — Daniel P. Morris, Esq.; Hoffmann & Baron, LLP (57) ABSTRACT

Methods and systems are provided for characterizing responses of a ligand-functionalized surface, which rely on dispensing a segmented liquid flow including liquid sequences, each including: an analyte segment including biomolecules of analyte; a spacer segment; and a wash segment including a washing liquid, whereby spacer segments separate wash segments from analyte segments in the dispensed segmented liquid flow. A measurement cycle is performed for each of the liquid sequences of the segmented liquid flow being dispensed. A measurement cycle includes: ejecting an analyte segment of each liquid sequence toward the ligand-functionalized surface and extracting, from each liquid sequence, a spacer segment succeeding the analyte segment as the latter is being ejected; ejecting a wash segment succeeding the extracted spacer segment in each liquid sequence to flush unbound and/or weakly bound biomolecules of analytes from the surface; and reading out a signal of bound biomolecules of analytes on the surface.

16 Claims, 4 Drawing Sheets

(51) Int. Cl.
*B01L 3/00* (2006.01)
*B01L 3/02* (2006.01)

(52) U.S. Cl.
CPC ... B01L 3/502746 (2013.01); B01L 3/502761 (2013.01); G01N 33/54366 (2013.01); G01N 33/54393 (2013.01); *B01L 2300/0627* (2013.01); *B01L 2300/0681* (2013.01); *B01L 2300/0838* (2013.01); *B01L 2300/0867* (2013.01); *B01L 2300/161* (2013.01); *B01L 2400/0487* (2013.01); *B01L 2400/082* (2013.01)

(58) Field of Classification Search
CPC .......... B01L 2400/022; B01L 3/50273; B01L 3/502761; G01N 33/54366; G01N 33/557
See application file for complete search history.

(56) References Cited

U.S. PATENT DOCUMENTS

| | | | |
|---|---|---|---|
| 9,316,636 B2 | 4/2016 | Karlsson et al. | |
| 2002/0028471 A1* | 3/2002 | Oberhardt | G01N 15/147 435/7.21 |
| 2007/0039866 A1* | 2/2007 | Schroeder | G01N 27/44769 210/265 |
| 2007/0059763 A1* | 3/2007 | Okano | G01N 33/566 435/7.1 |
| 2010/0116640 A1* | 5/2010 | Pamula | B01F 13/0071 204/156 |

OTHER PUBLICATIONS

Matthew A. Cooper, "Label-Free Screening of Bio-Molecular Interactions", Analytical and Bioanalytical Chemistry, Nov. 2003, vol. 377, Issue 5, (Abstract).

Hahnefeld et al., "Determination of Kinetic Data Using Surface Plasmon Resonance Biosensors," Methods in Molecular Medicine, vol. 94, pp. 299-320.

Bravman et al., "The Proteon XPR36TM Array System—High Throughput Kinetic Binding Analysis of Biomolecular Interactions", Molecular Interactions, Cellular and Molecular Bioengineering, Dec. 2008 (Abstract).

Ceccarini et al., "Biomolecular Interactions by Surface Plasmon Resonance Technology," Ann. 1st Super Sanita., 2005, 41(4), pp. 437-441 (Abstract).

* cited by examiner

CHARACTERIZING KINETIC RESPONSES OF A LIGAND-FUNCTIONALIZED SURFACE

BACKGROUND

The present invention relates generally to characterizing responses of ligand-functionalized surfaces and, more particularly, to microfluidic probes and the dispensation of segmented liquid flows by such microfluidic probes to characterize such responses.

A current standard technique used in measurements of biomolecular interactions and binding kinetics is the surface plasmon resonance (SPR) based analysis. This technique enables measurements of reaction kinetics of label-free reactants. It has, however, several disadvantages, among which include the following:

The distance between the bound receptor and the surface is limited to distances that are on the order of 200 nm. This limits the types of analyzed reactants to small molecules and does not allow accurate measurements using larger surface-bound ligands, such as cells (cell interactions can only be measured by using cells as the bulk analyte);

The SPR technique lacks sensitivity when measuring low molecular weight adsorbates;

SPR further requires a complex substrate, e.g., comprising a glass-metal film (typically the sensor chip is a gold-coated glass slide);

Due to its detection mechanism, the SPR method is limited to measurements of unique interactions and does not allow simultaneous kinetic measurements of multivalent interactions and competitive reactions;

The SPR technique requires specialized and expensive equipment, which may not always be affordable; and SPR is highly susceptible to temperature. Variations in temperature of less than 1 Kelvin can significantly impact the sensitivity of SPR.

An advance on the traditional SPR systems is the XPR system, or multiplexed SPR, which involves an array system of orthogonal and parallel channels. Different concentrations or analytes can thus be injected into each channel to create multiple pairings of reagents and conditions. While this improvement enables multiplexing in SPR, each measurement in the array corresponds to a unique interaction, i.e., measurements of competitive or multivalent interactions are not possible.

Labeled biomolecules (e.g., fluorescent, radioactive, chemiluminescent, etc.) are widely used in various biochemistry applications. Direct signal measurements can be performed using standard equipment, such as fluorescence microscopes and detectors, and therefore are commonly available in biology and research laboratories. However, real-time signal measurement of interactions between such molecules is limited by the background signal of the labeled analyte in the bulk, which is significantly higher than the signal of the bound analyte molecules.

Aside from SPR and XPR system, one knows microfluidic systems and related techniques, which deal with the behavior, precise control and manipulation of small volumes of fluids that are typically constrained to micrometer-length scale channels and to volumes typically in the sub-milliliter range. Prominent features of microfluidics originate from the peculiar behavior that liquids exhibit at the micrometer length scale. Volumes well below one nanoliter can be reached by fabricating structures with lateral dimensions in the micrometer range. Reactions that are limited at large scales (by diffusion of reactants) can be accelerated. Finally, parallel streams of liquids can possibly be accurately and reproducibility controlled, allowing for chemical reactions and gradients to be made at liquid/liquid and liquid/solid interfaces Microfluidic devices generally refer to microfabricated devices, which are used for pumping, sampling, mixing, analyzing and dosing liquids. A microfluidic probe is a device for depositing, retrieving, transporting, delivering, and/or removing liquids, in particular liquids containing chemical and/or biochemical substances. For example, microfluidic probes can be used in the fields of diagnostic medicine, pathology, pharmacology and various branches of analytical chemistry. Microfluidic probes can also be used for performing molecular biology procedures for enzymatic analysis, deoxyribonucleic acid (DNA) analysis and proteomics.

SUMMARY

According to a first aspect, the present invention is embodied as a method for characterizing responses of a ligand-functionalized surface. The method comprises dispensing a segmented liquid flow. The segmented liquid flow comprises liquid sequences, each comprising: an analyte segment comprising biomolecules of analyte; a spacer segment; and a wash segment comprising a washing liquid, whereby spacer segments separate wash segments from analyte segments in the dispensed segmented liquid flow. A measurement cycle is performed for each of the liquid sequences of the segmented liquid flow being dispensed. A measurement cycle comprises: ejecting an analyte segment of each liquid sequence toward the ligand-functionalized surface for the ejected analyte segment to interact with ligands on the surface and extracting, from each liquid sequence, a spacer segment succeeding the analyte segment as the latter is being ejected; ejecting a wash segment succeeding the extracted spacer segment in each liquid sequence, for the ejected wash segment to flush unbound and/or weakly bound biomolecules of analytes from the surface; and reading out a signal of bound biomolecules of analytes on the surface, to characterize a response of the ligand-functionalized surface.

According to another aspect, the invention is embodied as a characterization system for characterizing responses of a ligand-functionalized surface. The system comprises a liquid dispensation device, a liquid flow control unit, and a readout sensor unit. The liquid dispensation device, e.g., a microfluidic probe head, is configured to dispense a segmented liquid flow that comprises liquid sequences, each comprising: an analyte segment comprising biomolecules of analyte; a spacer segment; and a wash segment comprising a washing liquid, whereby spacer segments separate wash segments from analyte segments in the dispensed segmented liquid flow. The liquid flow control unit is operatively connected to the liquid dispensation device so as, for each liquid sequence of the segmented liquid flow to be dispensed via the liquid dispensation device, to eject and extract liquid segments, according to principles evoked above. The readout sensor unit is configured in the system for reading out a signal of bound biomolecules of analytes on the surface, to characterize a response of the ligand-functionalized surface.

Devices, apparatuses, systems and methods embodying the present invention will now be described, by way of non-limiting examples, and in reference to the accompanying drawings.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION OF EMBODIMENTS OF THE INVENTION

The present invention, in accordance with one or more embodiments thereof, provide simple and non-expensive methods and systems for measuring (preferably in real-time) interactions between labeled biomolecules, which can find applications in biological and chemistry research, medical diagnostics, immuno- and hybridization assays, e.g., where kinetic profiling of interactions between biomolecules is desired.

Figure 1:
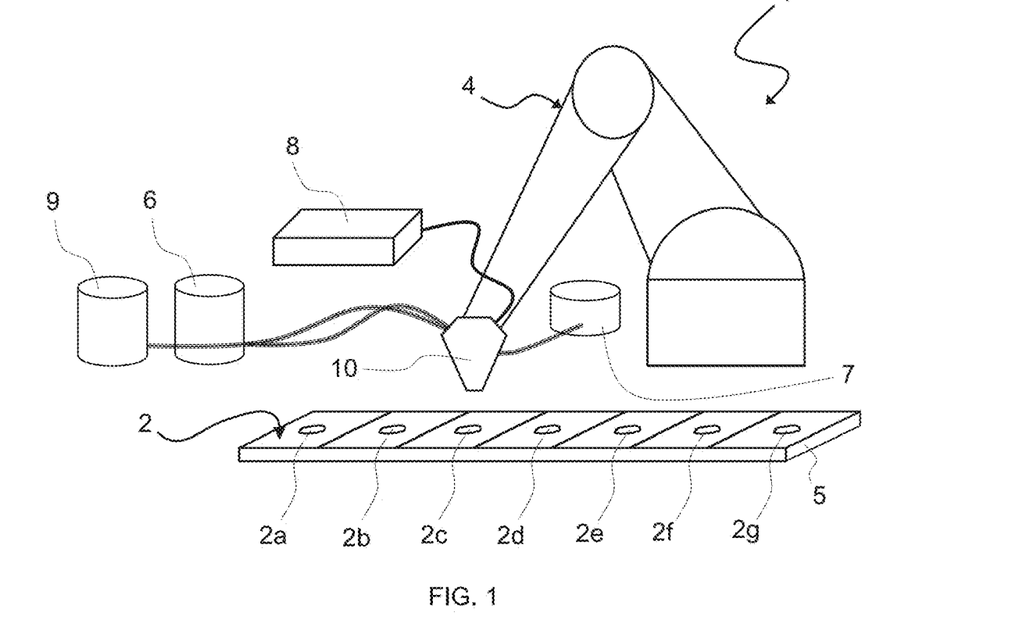
FIG. 1 is a view of a microfluidic probe system, according to embodiments.
Figure 2:
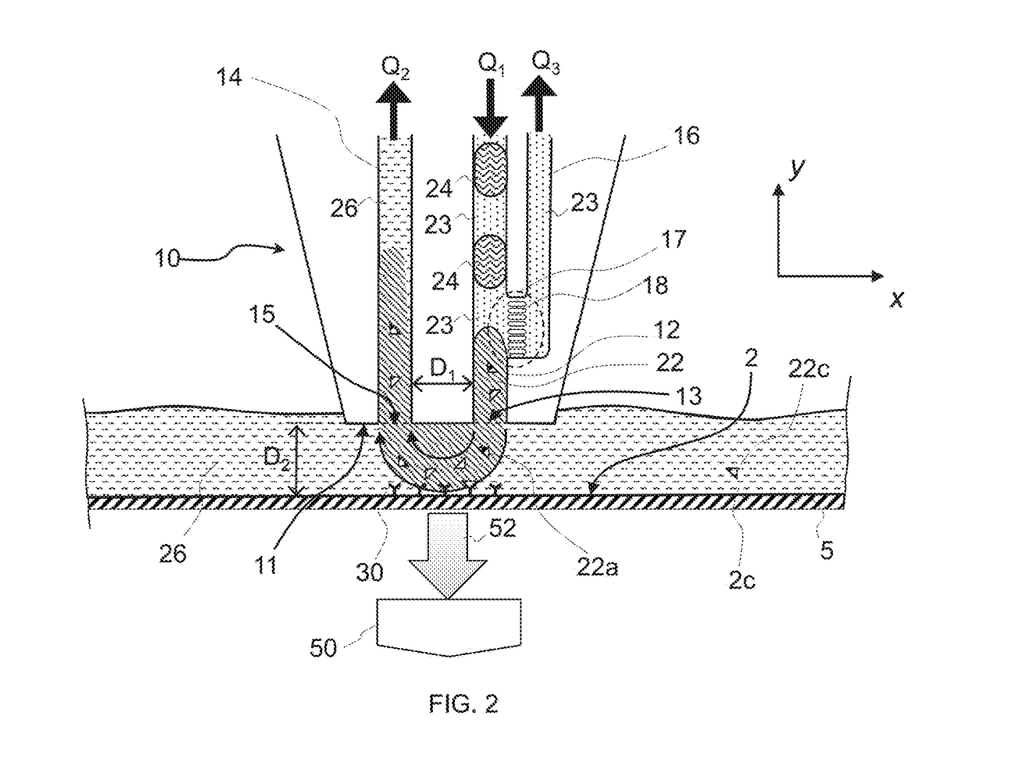
FIG. 2 is a cross-sectional (partial) view of a microfluidic probe head as used in a system such as depicted in FIG. 1 to characterize responses of a ligand-functionalized surface, as in embodiments.

In reference to FIGS. 1-3, an aspect of the invention is first described, which concerns methods for characterizing responses of a ligand-functionalized surface 2. Such methods rely on dispensing a segmented liquid flow. This segmented liquid flow involves several sequences of liquid segments 22, 23, 24. The sequences may for instance repeat identically, or not. In all cases, each liquid sequence includes at least:

An analyte segment 22, which comprises biomolecules of analyte, which are typically suspended in a polar, e.g., aqueous, liquid. Analyte can for instance be proteins, antibodies, DNA, RNA or cells, which are likely to interact with ligands on the surfaces 2. Biomolecules are preferably labelled (e.g., fluorescent, radioactive, chemiluminescent, etc.) for detection purposes;

A spacer segment (also referred to as "spacer" or "liquid spacer") 23, which may comprise, e.g., a nonpolar liquid and/or a nonpolar solvent, e.g., a fat, an oil, a lipid, hexane or toluene oil. Oil spacers are preferred, as assumed in the following; and A wash segment 24, which comprises a washing liquid, e.g., based on a polar liquid such as a liquid comprising water and/or a solvent.

That is, each liquid sequence includes at least a sequence of liquid segments 22-23-24, or possibly more complex arrangements of segments, e.g., segments 22-23-24-23-24-23 . . . , as in the case of FIG. 2, where the segment 22 is the first one to be dispensed in that case. Oil segments 23 separate wash segments 24 from analyte segments 22 in the dispensed segmented liquid flow; that is, there is at least one oil segment 23 between an analyte segment 22 and a wash segment 24 and at least one oil segment 23 between this wash segment 24 and an analyte segment 22 of a next sequence. In fact, each liquid sequence may comprise one or more analyte segments 22, one or more oil segments 23 and one or more wash segments 24.

Figure 3A:
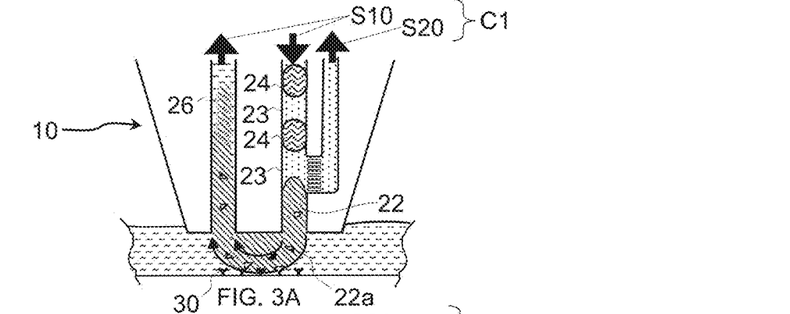
FIGS. 3A-3D are cross-sectional views of a device similar to that of FIG. 2, where the views illustrate steps of a method for characterizing responses of a ligand-functionalized surface, according to embodiments.
Figure 3B:
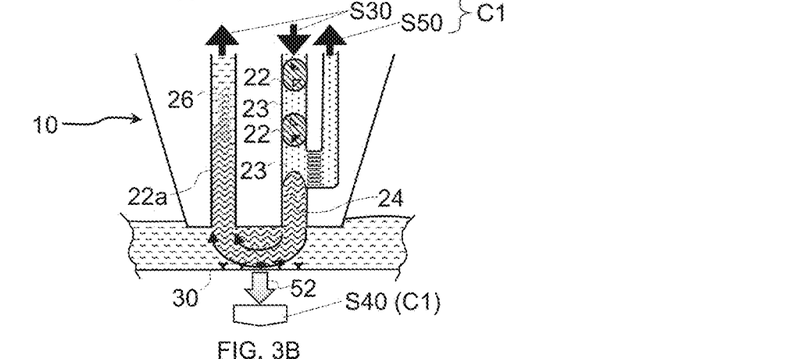
Figure 3C:
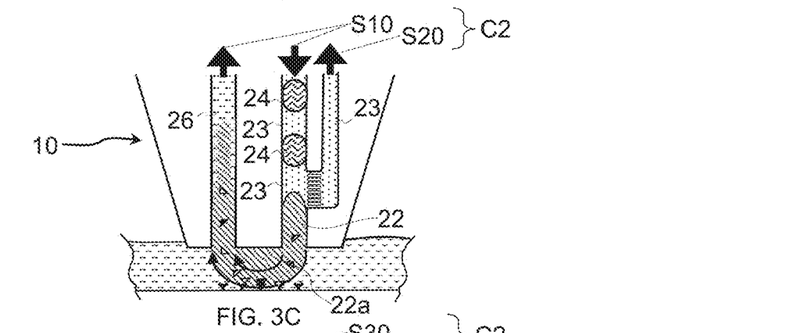
Figure 3D:
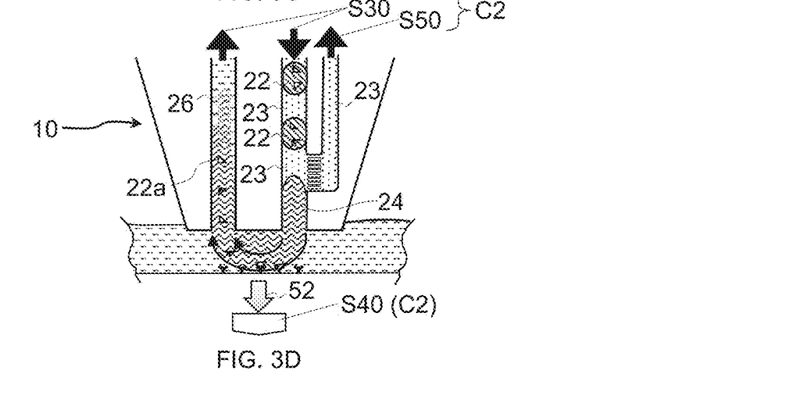

According to present methods, a specific measurement cycle is performed for each liquid sequence 22-23-24 . . . of the segmented liquid flow that is dispensed. Thus, several measurement cycles C1, C2, . . . , are performed, as illustrated in FIGS. 3A-3D. Each measurement cycles C1, C2, . . . , comprises a series of steps S10-S40, which decomposes as follows:

First, an analyte segment 22 of a current liquid sequence is ejected S10 toward the ligand-functionalized surface 2. The ejected analyte segment 22 interacts with ligands 30 on the surface 2, which may give rise to bound biomolecules of analytes on the surface 2;

The oil segment 23 that succeeds the analyte segment 22 in the current sequence is extracted S20 from the current liquid sequence. Steps S10 and S20 are at least partly concomitant as the oil segment 23 starts being extracted while the analyte segment 22 is still in the process of being ejected, as illustrated in FIG. 3A;

Then, once the ejection of the analyte segment 22 has completed and the oil segment 23 is extracted, a wash segment 24 is ejected S30, which segment 24 was initially separated from the analyte segment 22 by the previously extracted oil segment 23. The ejected wash segment 24 serves to flush unbound and/or weakly bound biomolecules of analytes from the surface 2, as illustrated in FIG. 3B. In the (pedagogical) example of FIG. 3B, only one (firmly) bound biomolecules of analytes is assumed to remain on the surface 2, after flushing S30; and Finally, a signal 52 of the remaining, bound biomolecules of analytes on the surface 2 can be read out S40, so as to characterize a response of the ligand-functionalized surface 2. The ligands need not be uniformly distributed on the surface 2. They may instead form spots, like microarrays, and the read out measurements can accordingly be done at several sites, as assumed in FIG. 1 or FIG. 8.

In practice, the ejected washing liquid segment happens to flush molecules of analyte that are loosely bound, or not bound at all, i.e., molecules that are insufficiently bound, while remaining molecules can be read out. Removing unbound or weakly bound analytes from the surface 2 with the wash buffers 24 makes it possible to remove background signal from the readouts.

Possible characterization techniques may use, e.g., fluorescence, radioactivity detection, chemiluminescent, or more generally any kind of electro-magnetically labelled molecules. One or more optical detectors or Geiger counters can for instance be used.

Steps S10, S20 are typically concomitant (at least partly). Steps S30 and S40 are preferably (at least partly) concomitant, for reasons explained later. As seen in FIG. 3B, a further oil segment extraction S50 will typically occur to extract a next oil segment 23 that separates the wash segment that is being ejected in FIG. 3B from a next analyte segment 22 of the next sequence. Step S50 may be at least partly concomitant with step S30, for the same reasons that steps S10 and S20 are. Thus, step S50 could also be at least partly concomitant with the detection step S40.

In other words, the present methods rely on a segmented liquid flow, whose oil segments are extracted during the liquid deposition process. This, in turn, allows rapid flow switching between analytes and wash buffers. As wash buffers further allows background signal to be removed from the readouts, the present approach provides a simple, non-expensive method, allowing fast (e.g., real-time) and clean measurements of interactions between biomolecules.

As discussed later in detail, present methods can notably be used to characterize dissociation kinetics, by switching the analyte solution to the wash buffer and performing detection while rinsing the surface. That is, the wash buffers can be dimensioned so as to rinse the surface during a sufficiently long time for the bound analytes to dissociate, while monitoring signals 52 from the surface 2. Since the time for switching the analyte solution to the wash buffer can be made small compared to the rinsing time during which signals 52 are monitored, present methods can be used to characterize kinetic responses with time constants much longer than the switching time.

Figure 7:
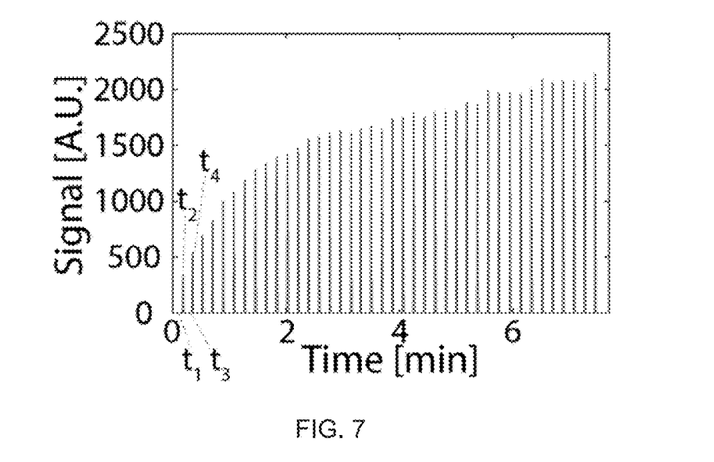
FIG. 7 is a plot representing a biomolecular kinetic profile as obtained according to embodiments of the present methods.
Figure 8:
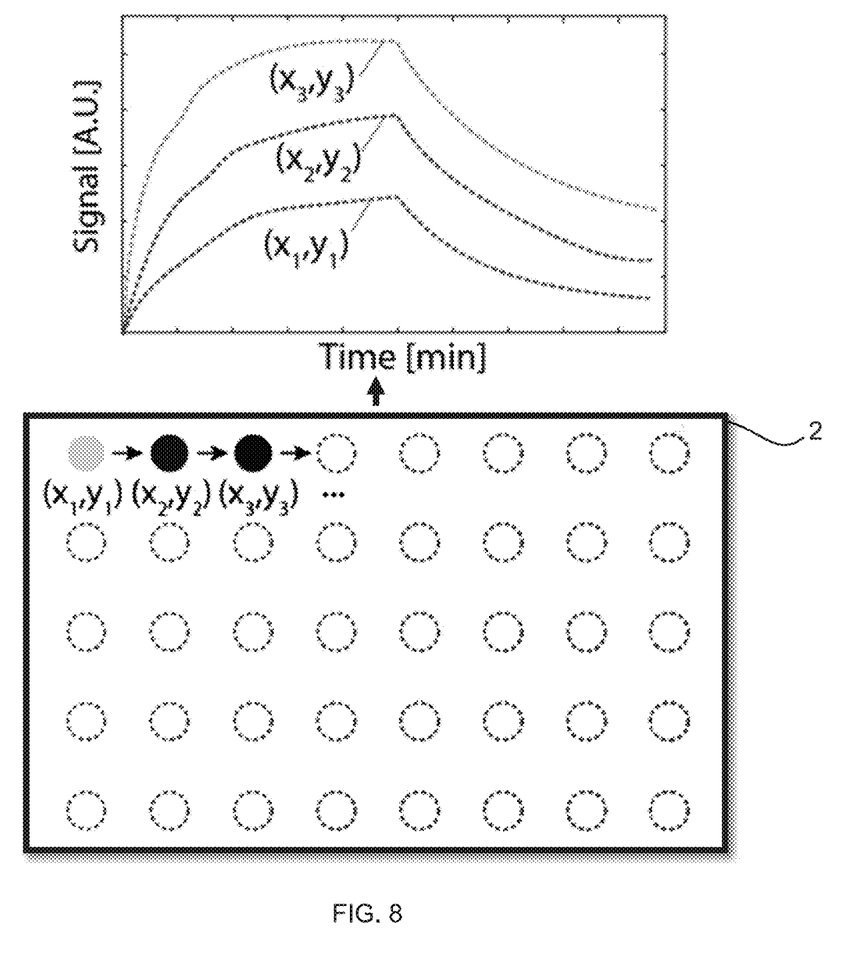
FIG. 8 shows a functionalized surface having multiple reaction sites (lower figure) and corresponding kinetic profiles as obtained according to embodiments of the present methods.

For example, and as illustrated in FIGS. 3A-3D, 7 and 8, signals 52 can be read out S40 at each measurement cycles (possibly several times during a same measurement cycle), so as to characterize a biomolecular kinetic response of the ligand-functionalized surface 2. This response can for instance be characterized as a kinetic profile, such as depicted in FIG. 7 or FIG. 8. To that aim, interaction times of the analyte segments 22 with ligands on the surface 2 may need be taken into consideration, in addition to signals 52 read out at step S40.

Moreover, embodiments of the present invention allow the sample to be delivered to the surface 2 in a non-contact scanning mode, using a microfluidic probe head (hereafter "MFP head"), thus allowing multiple reaction spots on the surface 2. Full multiplexing can be contemplated, by monitoring multiple reaction sites on a surface. This can be achieved by using multiple MFP heads and detectors, or by scanning one or more heads over the surface 2.

In addition, present methods allow binding data to be collected for multivalent or competing reactions simultaneously, with real-time analysis. For multivalent and competitive interactions, which occur on a same spot and at the same time, different labels (e.g., fluorescent) can be read out. For example, different wavelength filters can be used to monitor a reaction with a mixed analyte solution. Reaction kinetics of multivalent or competing reactions (on a same microspot) can thus be determined and direct measurements of kinetic parameters of labeled reactants are possible.

As the present methods do not require an SPR system, the size of the analytes is not limited and thus analysis of reactions taking place at distances larger than about 200 nm from the sensor surface 2 is possible. Also, several detection mechanisms (other than SPR, e.g., based on fluorescent labels) can be contemplated.

Referring more particularly to FIG. 2: the ligand-functionalized surface 2 is preferably the surface of a layer 5 that is permissive to light, i.e., transparent at wavelengths at which labels are active, to enable backside detection. That is, the analyte segment 22 and wash segment 24 are ejected toward the surface 2 on one side of layer 5, whereas signals 52 are read out S40 from the opposite side, at each measurement cycle. The surface 2 can for instance be a glass layer 5 or a plastic layer, or any transparent material.

In addition, performing detection from the opposite side of layer 5 is practical as detection does not hinder the liquid deposition process, which allows detection and liquid ejection to be at least partly concomitant and thus allows high-speed measurement cycles.

Preferably, and as illustrated in FIG. 3, signals 52 are read out S40 while flushing S30 unbound and/or weakly bound biomolecules of analytes from the surface 2, thanks to the ejected wash segment 24 and, this, at each measurement cycle C1, C2, . . . . I.e., steps S30 and S40 are thus at least partly concomitant, as illustrated in FIGS. 3B and 3D. As noted earlier, steps S30 and S40 may further be at least partly concomitant with step S50, during which another oil segment 23 is extracted, which separates the wash segment 24 (being currently ejected) from the next analyte segment 22, in view of a next measurement cycle.

The time duration of S10 (during which the analyte 22 is in contact with the surface 2) may typically be of a few seconds or minutes, e.g., between 1 s and 3 min. Yet, the time duration of step S30 (during which the surface 2 is rinsed by the wash buffer 24) is preferably of a few seconds only, e.g., between 1 and 10 seconds each, for example of 5 seconds. The rinsing time should be adjusted according to the off-rate of the measured reaction to remove any unbound molecules and detect S40 the results of the interaction on the surface 2.

Thanks to the segmented liquid used and the extraction of oil segments, no time is lost for switching. If necessary, the flow rates as used at steps S10-S50 can be varied in time. An optical monitoring system (not depicted) may further be used to monitor incoming liquid segments and provide feedback to a control unit, which, e.g., varies pressures applied to obtain suitable, timely flow rates and enable the desired sequences. The flow rates applied are preferably constant, be it to main a stable segmented liquid flow. If necessary, a synchronization process is implemented, to synchronize measurements with rinsing liquid segments applied on the surface 2.

Both the liquid segment lengths and flow rates can be jointly refined prior to performing measurement cycles. Well-calibrated segment lengths and flow rates make it possible to investigate kinetic responses with large time constants, e.g., much longer than the time necessary for oil extraction (i.e., for switching between analyte solutions and wash buffers).

As seen in FIGS. 2-6, one or more of the liquid sequences used may, in embodiments, comprise (each): a plurality of successive wash segments 24. The successive wash segments 24 comes one after the other in a same sequence, although they are separated by oil segments 23. Oil segments 23 are otherwise used to separate, on the one hand, an analyte segment 22 from a first wash segment 24 and, on the other hand, a last wash segment 24 from an analyte segment 22 of a next sequence. At each measurement cycle, oil segments 23 are extracted S20 throughout the process, i.e., before, while or after an analyte segment 22 or a wash segment 24 is ejected. It may be preferred to use several wash segments in a same sequence (i.e., during a same measurement cycle) to flush the surface 2. In that case, several detection steps may be carried out and synchronized with the rinsing phases to enable kinetic profiling, after one type of analyte 22 has interacted with the surface 2.

Preferably, the analyte segments 22 comprise labelled biomolecules 22a-22c of analyte, to ease detection. More generally, analyte segments of one or more of the liquid sequences 22-23-24 may be labelled. Labeled biomolecules (e.g. fluorescent, radioactive, chemiluminescent, etc.) are widely used in various biochemistry applications. Advantageously, the present methods allows biomolecules of analyte to be labelled a priori.

Figure 4:
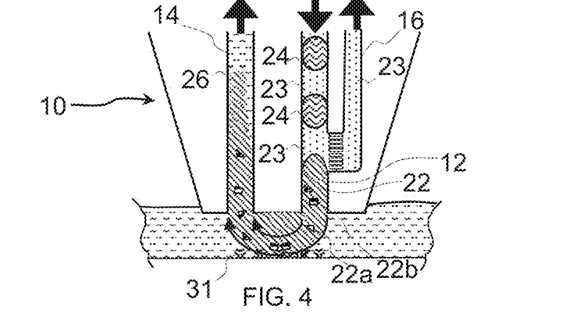
FIGS. 4-6 are cross-sectional views of a microfluidic probe head similar to that of FIG. 2, as used in variants to the methods of FIGS. 3A-3D.

Referring now to FIG. 4: in embodiments, one or more of the liquid sequences 22-23-24 of the dispensed liquid flow may comprise, each, analyte segments 22 with distinct types 22a, 22b of labelled biomolecules of analyte. In that case, the ligand-functionalized surface 2 may comprise distinct types of receptors, or multivalent receptors 31, with which the distinct types of labelled biomolecules of analyte may interact, as illustrated in FIG. 4. The distinct types of labels allows signals of distinct types of labelled biomolecules to be read out at steps S40. This way, kinetic profiling of multivalent or competitive interactions is made possible. For instance, interactions with multiple receptors and analytes can be screened and profiled simultaneously using different fluorophores. Such an option is advantageous where competitive reactions are involved, in which the presence of additional analyte molecules affects the reaction rate of an analyte of interest. Still, a direct measurement of the rate of the reaction of interest is possible, thanks to the use of multiple receptors and analytes.

As it can be realized, such embodiments make it possible for multivalent interactions to be measured more efficiently, allowing parallel measurement using different fluorescence filters in place of a sequence of separate measurements. For example, multivalent interactions are critical for protein interactions on cell surfaces, where multiple ligands on one cell bind to multiple receptors on another. These interactions function collectively, govern immune responses and activate cell signaling pathways. Embodiments of the present methods may thus find application in drug research, e.g. for virus inhibition.

Figure 5:
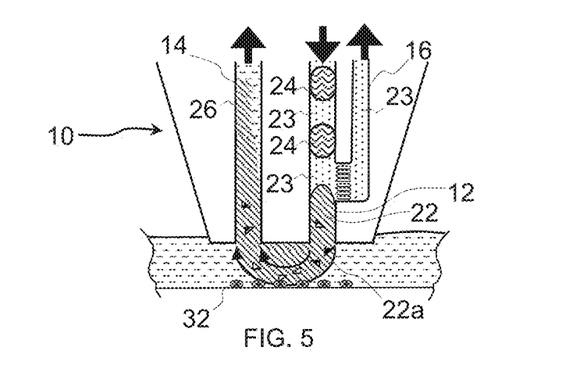
Figure 6:
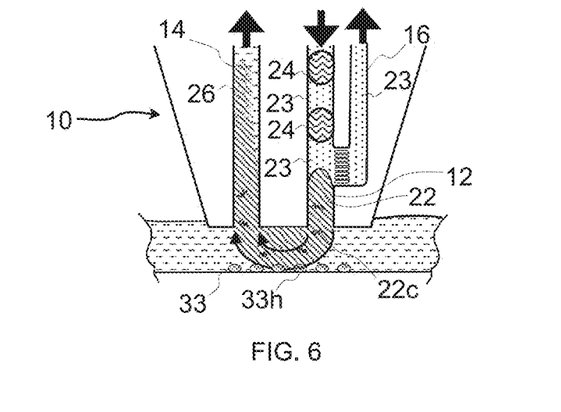

Referring now to FIGS. 5 and 6: in embodiments, the ligand-functionalized surface 2 may comprise cells and/or nuclei 32, 33 patterned thereon, and, this, so as to be immobilized on the surface 2, e.g., by using adherent cells. Biomolecules 22a or 22c may interact with such cells and/or nuclei 32, 33 when ejected toward the surface 2. Subsequent detection allows the outcome of such interactions to be monitored according to principles evoked earlier.

For example, referring to FIG. 6, the ligand-functionalized surface 2 may, in embodiments, comprise cells 33 patterned thereon. Analyte segments 22 of (one or more) of the liquid sequences 22-23-24 of the dispensed liquid may comprise a probe solution 22, so as for ejected probes 22c (e.g., antibodies, cells, etc.) to interact with targets 32, 33 on the surface 2. In particular, nucleic acid interactions may take place on the surface and the subsequent detection may be performed so as to characterize a biomolecular kinetic response of hybridized cells 33h on the surface 2.

Quantifying antibodies-cells or cell-cell interactions in a configuration where cells 33 are immobilized on surface is a major challenge when using SPR-based techniques. Since, here, embodiments of the present methods can be purely based on fluorescence (or similar optical detection techniques), the detection is not limited by the distance between the detector and surface 2 or by the molecule size (typically of 1-50 μm. Responses on the scale of a single-cell length can even be recorded, especially when using a microfluidic probe to dispense the segmented liquid flow, as discussed later in detail. Applications to kinetic profiling of intracellular hybridization assays can thus be contemplated.

As assumed in the embodiments of FIGS. 1-6, the present methods may advantageously make use of a MFP head 10. I.e., the steps of ejecting S10 the analyte segment 22, extracting S20 the oil segment 23 and ejecting S30 the wash segment 24 are all performed using the MFP head 10, with the latter positioned opposite to the surface 2.

The distance $D_2$ (FIG. 2) between the processing surface 11 of the head and the surface 2 will typically depend on the types of liquids used, their flow rates, the size of the apertures and the distance between such apertures.

Using a MFP system is advantageous inasmuch as it can be used to scan the surface 2 with a MFP head 10. For instance, referring to FIG. 1, the MFP head 10 may be scanned over a ligand-functionalized surface 2 and operated so as to eject analyte segments 22 (of distinct sequences) toward the surface 2, at distinct locations 2a-2g of this surface. Thus, the ejected analyte segments 22 will interact with ligands at the distinct locations. Several interaction sites may thus be monitored in parallel. Distinct analyte segments 22 and/or receptors on the surface 2 may be relied on, to analyze distinct reactions in parallel.

The MFP head 10 may in principle be of the "horizontal" type (not shown) or the "vertical" type, as assumed in FIGS. 1-6. Using vertical MFP heads is preferred because of their easier fabrication (microchannels are provided at an interface between two superimposed layers), as discussed later in detail.

The MFP head 10 is preferably designed as shown in FIG. 2. Namely, it comprises an ejection channel 12 and an oil extraction channel 16. The ejection channel 12 leads to an ejection aperture 13 on the processing surface 11 and the oil extraction channel 16 joins the ejection channel 12 at a junction 17. This junction 17 comprises a capillary array 18, where the array includes hydrophobic capillary structures. The latter are designed so as to impose a given capillary pressure on aqueous liquids. However, the capillary pressure as experienced by oil will be different, such that oil segments 23 may overcome this pressure when reaching the junction 17, while aqueous segments 22, 24 will typically not, provided other conditions are met, see below.

This MFP head can be operated as follows (see FIGS. 3A-3D). The processing surface 11 is brought into a position opposite the surface 2 and the segmented liquid flow is dispensed via the ejection channel 12. At each measurement cycle C1, C2, etc., performed, an oil segment 23 is extracted S20 via the oil extraction channel 16, as the latter is subject to a lower pressure than the capillary pressure caused by the capillary array 18. As a result, oil segments 23 get filtered through the hydrophobic capillary structures of the array, while analyte segments 22 and wash segments 24 are maintained in the ejection channel 12 and ejected S10, S30 via the ejection aperture 13. Thus, the capillary structure 18 acts as a valve and only the analyte and wash segments 24 are ejected via the ejection aperture 13. Although the capillary structure will somewhat impacts the processing time, the switching time may be made smaller than the time during which segments 22, 24 will process the surface 2, if necessary.

In embodiments as depicted in FIGS. 2-6, the MFP head 10 used further comprises an aspiration channel 14 leading to an aspiration aperture 15 on the processing surface 11. In operation, the surface 2 is immersed in an immersion liquid 26. The aspiration channel 14 is therefore used to aspirate liquid via the aspiration aperture 15, while dispensing the segmented liquid flow. The aspirated liquid may typically include some of the immersion liquid 26, as well as some of the ejected liquids 22, 24. Using a configuration of apertures and conduits 12-15 as depicted in FIG. 2 allows laminar viscous liquid flows and, in particular, hydrodynamic flow confinements, to be achieved. This is discussed later in detail.

The surface 2 can be scanned using a MFP head 10, to dispense (typically distinct types of) analyte segments 22 at distinct locations on the surface 2. In more sophisticated scenarios, two or more liquid sequences may be dispensed (at different times), at distinct locations 2a-2g on the surface 2, for which distinct measurement cycles are performed. That is, a measurement cycle may be performed for each liquid sequence dispensed and at each location on the surface. This way, the present methods can be multiplexed, using several MFP heads 10 in parallel or using one MFP head successively and repeatedly brought at the different locations (as in FIG. 1), to study concurrent dynamics of different reactions.

For instance, FIG. 8 shows an array of target sites defined on a surface 2, for which reaction kinetics can be concurrently monitored, whereby distinct curves are obtained for the distinct locations on the array.

So far, methods for characterizing responses of a ligand-functionalized surface have been described. Still, another aspect of the invention relates to a characterization system 1, which can be used to perform such methods. An example of such a system is shown in FIGS. 1 and 2.

Most generally, such a system comprises a liquid dispensation device 10, which is configured to dispense a segmented liquid flow 22-23-24 as described earlier. The system 1 further comprises a liquid flow control unit 8, which is operatively connected to the liquid dispensation device 10 to allow liquid dispensation. I.e., for each liquid sequence, the control unit 8 cooperates with the dispensation device 10 to eject analyte segments 22 and wash segments 24, while extracting intermediate oil segments 23. Furthermore, the system 1 comprises a readout sensor unit 50, which is configured to read out signals 52 of bound biomolecules of analytes on the surface 2, so as to characterize a response of the ligands, according to principles described earlier.

In embodiments, the liquid dispensation unit comprises a MFP head 10, having microchannels 12, 14, 16 provided therein, as discussed earlier. The liquid flow control unit 8 may for instance be operatively connected to pumping means connected to the MFP head 10 to apply pressures to the microchannels 12, 14, 16 and obtain suitable flow rates, to implement methods as contemplated herein.

For example, and as described earlier in reference to FIG. 2, the MFP head 10 may exhibit a processing surface 11, an ejection channel 12 leading to an ejection aperture 13 on the processing surface 11, as well as an oil extraction channel 16 joining the ejection channel at a junction 17, the latter comprising a capillary array 18 with hydrophobic capillary structures. In that case, the liquid flow control unit 8 is configured to apply to the oil extraction channel 16 a pressure lower than a capillary pressure caused by the capillary array for extracting oil segments 23 from the liquid sequences in the ejection channel 12 via the oil extraction channel 16. This way, oil segments 23 get filtered through the hydrophobic capillary structures 18, while analyte segments 22 and wash segments 24 are maintained in the ejection channel 12, for ejection via the ejection aperture 13, in operation.

Moreover, the MFP head 10 may further comprise an aspiration channel 14 leading to an aspiration aperture 15 on the processing surface 11. In that case, the control unit 8 may further be configured to apply pressure to the aspiration channel 14, so as to aspirate liquid, while otherwise dispensing liquid through the ejection aperture 13 and filtering oil segments via the junction 17, in operation.

For instance, in preferred embodiments, the diameters of each of the channels 12, 14 and their respective apertures are between 25 and 100 µm, e.g., substantially equal to 50 µm. Lateral gaps (along axis y) between capillary structures of the array at the junction 17 are between 10 and 30 µm, e.g., substantially equal to 15 µm, while the width (along axis y) of such capillary structures is typically between 10 and 40 µm, e.g., substantially equal to 20 µm. The minimal gap between channels 12 and 16 (along axis x) is typically between 50 and 200 µm, e.g., substantially equal to 100 µm. The minimal distance $D_1$ between the first and second apertures is between 1.0 µm and 2.0 mm, and preferably between 50 and 100 µm.

In addition, the junction 17 is, by design, necessarily recessed (along axis y) with respect to the processing surface. This recess should be as small as possible in practice, to avoid intermixing of segments 22 and 24 after extraction. The recess distance is preferably between 100 and 400 µm, e.g., substantially equal to 200 µm, in practice.

As seen in FIG. 1, various liquid supplies 6, 7 and 9 may be fluidly connected to (i.e., in fluid communication with) the ejection channel 12 of the head 10. To that aim, suitable insertion junctions or valves (not shown) may be needed, either outside the head 10 or, in variants, directly on the head 10. Each liquid supply 6, 7, 9 may be fluidly connected to the ejection channel 12 via respective insertion junctions, for inserting corresponding segments 22-24 therein.

A modulation unit (not shown) may be provided, which automatically controls insertions of the various liquid segments via insertion junctions or valves. This modulation unit may form part of the control unit 8. As a result, liquid volumes 22, 24 can be obtained, which are separated by the oil spacers 23 inserted in-between. This modulation unit may further be configured to modulate the lengths of inserted liquid segments, if necessary. The inserted liquid segments 22-24 may thus be modulated (in terms of lengths of the segments and/or numbers of inserted segments), as needed for the desired type of experiments. The liquid sequence is preferably formed and buffered outside the head 10 and delivered to it via tubes and tubing ports connected to the head 10.

One or more detection units (not shown) may be arranged upstream or downstream an insertion junction or an insertion valve (upstream the junction 17), to enable or improve the synchronization of the liquid segment insertion.

The MFP system 1 may comprise a positioning system 4. The positioning system is preferably configured for positioning the probe head 10 in x, y, z, so as to bring the head 10 at processing distance from the surface 2 and adjust its position above the surface 2. In addition, the positioning system may transmit position data for said given positions, to synchronize the detection steps S40. Also, the modulation unit may be appropriately connected to the positioning system 4 so as to modulate the insertion of liquid segments 22-24 according to position data transmitted by the positioning system, if needed.

FIG. 1 shows a view of a MFP system 1 for sequentially dispending substances on respective target areas 2a-2g of the surface 2. The head 10 is connected to the positioning device 4, here a robotic arm 4. Additionally, the probe head 10 and/or the robotic arm 4 may be arranged on a movable stage. The probe system 1 should otherwise preferably be configured to arbitrary three-dimensional movement. In FIG. 1, the robotic arm 4 allows the MFP head 10 to be positioned at a specific location and, in particular, above each of the target areas 2a-2g that are typically arranged in an array.

In the embodiment of FIG. 1, injection liquid supplies 6, 9 and an oil spacer supply 7 are, each, in fluid communication with the probe head 10. The injection liquid supplies 6, 9 supply the probe head 10 with injection liquids. The oil supply 7 provides spacer fluid. Pressure sources (not shown) are further provided, to enable insertion and/or aspiration of liquid from the supply units 6, 7, 9. Suitable pressure sources for microfluidics are known per se, as well as control units to operate them.

Referring to FIG. 2, present MFPs 10 will likely include three or more channels 12, 14, 16. Notably, the probe head 10 comprises a first channel 12 in fluid communication with a first aperture 13 on the processing surface 11, for ejecting liquid toward the surface 2. The head 10 further comprises a second channel 14 and a second aperture 15, e.g., to aspirate liquid. The first aperture 13 and the second aperture 15 are dimensioned and positioned at a distance so as to make it possible for the probe to re-aspirate at the second aperture 15 liquid that comprises processing liquid delivered through the first aperture 13. I.e., assuming given diameters for the apertures, an appropriate distance between the apertures may be imposed so as to make it possible for the probe to aspirate at the second aperture 15 liquid that notably comprises some of the processing liquid 22, 24 delivered through the first aperture 13.

To that aim, the probe 1 may be configured to achieve hydrodynamic flow confinement (HFC) of the processing liquid 22, 24. Generally speaking, HFC relates to a laminar viscous flow of liquid, which is spatially confined within an environmental liquid (or immersion liquid), into which the processing liquid is injected.

To that aim, the channel 12 is used to inject liquid segments 22, 24 into the liquid bath 26 with a given injection flow rate and the microchannel 14 aspirates part of the previously injected liquid and some of the background liquid 26 with a given aspiration flow rate. By keeping the aspiration flow rate higher than the injection rate, e.g., at a defined ratio, a laminar flow path of processing liquid can be formed and confined within the immersion liquid 26.

In the embodiment of FIG. 2, the target area is defined on the surface 2 of, e.g., Petri dish, which is filled with immersion liquid 26, so that the target area is immersed in the immersion liquid 26.

The MFP head 10 comprises a body having a processing (end) surface 11. The channels 12, 14, 16 are, each, formed in the body. All the channels 12, 14, 16 are preferably formed at an interface of two layers (e.g., by grooving a silicon substrate and closing it with a lid), according to the concept referred to as "vertical MFP head" in the literature, which simplifies the fabrication of the heads. The first 13 and second 15 apertures are, each, defined on the processing surface 11 of the body of the head 10 and fluidly connected to the first and second liquid channels 12, 14, respectively. For example, a minimal distance $D_1$ between the first and second apertures may be between 0.5 μm and 2 mm, and preferably between 1.0 and 100 μm.

The body of the MFP head 10 acts as housing or carrier. All elements, parts and/or devices integrated in the body 12 may be manufactured on-chip (using standard lithography processes, for example) and are movable therewith.

In FIG. 2, the MFP head 10 is positioned above a target area. The processing surface 11 of the MFP head 10 is placed at a distance $D_2$ above the target area, so as for the processing surface 11 to be immersed in the immersion liquid 26 that covers the target area. For example, the distance $D_2$ may be of 1-100 μm, and preferably 2-80 μm, depending on the size of target molecules 30-33 on surface 2 and the intended size of the HFC.

The segmented liquid flow is delivered via the first channel 12 to the first aperture 13 with a first flow rate $Q_1$. A negative pressure is applied to the second liquid channel 14 such that some of the immersion liquid 26 and the ejected liquid 22, 24 can be aspirated through the second aperture 15 with a second flow rate $Q_2$. The first and second flow rates $Q_1$, $Q_2$ may be generated using respective, active pumps (not shown), which are known per se.

Provided a specific ratio of $Q_2$ to $Q_1$ is maintained (e.g., 1.2-10, preferably 2-4), a laminar flow path of processing liquid from the first 13 to the second 15 aperture can be obtained. Achieving such a laminar flow allows for hydrodynamic flow confinement. I.e., the laminar flow is hydrodynamically confined by the immersion liquid 26 within a confinement volume that extends from below the first aperture 13 to below the second aperture 15. The size of the confinement volume and the shape of the laminar flow are notably determined by the flow rates $Q_1$ and $Q_2$, the ratio of $Q_2$ to $Q_1$, $D_1$ and, in a less extent, $D_2$.

The flow rates $Q_1$ and $Q_2$, the ratio of $Q_2$ to $Q_1$ and the distance $D_2$ are parameters that depend on the operation method chosen. Assuming given dimensions for the apertures 13, 15, the main parameter that remains to be fixed is the distance $D_1$. In practice, the average diameter of the apertures may typically be between 0.5 and 1000 μm (at the level of the end surface 11). The ejection aperture 13 may, however, be designed small enough to enable a very local liquid confinement. Such a confinement (of e.g., 150 μm) is best obtained with a diameter of the ejection aperture 13 of about 20 to 50 μm. It can still be fabricated substantially smaller, e.g., 0.5 μm, which may be useful in some specific applications. The apertures 13, 15 end, each, a respective conduit (forming respective channels 12, 14) having preferably the same average diameter as their respective apertures. Yet, the sizes of the apertures 13, 15 may differ from each other (e.g., small outlet, large inlet). The aspiration aperture 15 may, in some cases, be much larger than the expected confinement size, especially where one seeks to prevent clogging by particles/dust. The dimensions retained for the apertures and their asymmetry strongly depends on the application sought. The flow characteristics enabled by the indicative dimensions given above are nevertheless suited for a wide range of applications. In particular, the distance $D_1$ between the apertures 13, 15 is preferably more than 5 μm, but also less than 2 mm. The diameter of the opening shall typically be small (typically one order of magnitude below, or more) compared to the distance $D_1$. With such dimensions, a stable confinement can in principle be achieved, while remaining practical from the fabrication standpoint.

Regarding the flow rates: for example, $Q_1$ may be chosen to be 1.0 fL/s-1.0 mL/s, and preferably 1.0-50 nL/s, while $Q_2$ may for example be chosen to be 1.2 fL/s-10 mL/s, preferably 2.0-200 nL/s.

The ejected liquids 22, 24 typically comprise polar liquids, in particular water-based or water-soluble liquids. On the contrary, the spacer fluid 23 will comprise a fluid that is immiscible with the liquids to be ejected. In particular, the spacer fluid 23 can comprise a nonpolar liquid and/or nonpolar solvent, e.g. a fat, an oil, a lipid, hexane or toluene.

As evoked earlier, detection units may be arranged inside the body of the head 10, to enable liquid detection inside a detection volume of the first channel 12. Such detection units, in turns, allow to measure one or more properties, e.g. a surface tension, a refraction index, a pH, a heat conductivity, an electrical conductivity, a viscosity, an impedance, a temperature and/or an inductance, of liquid passing through the detection volume.

This way, separate liquid volumes can be sensed and identified locally, i.e., directly at the level of channel 12. Upon identifying separate liquid volumes, the detection units may generate a detection signal and transmits it to the insertion units, to help synchronizing the liquid segment insertion, if necessary. A modulation unit controls the insertion rate, at which the liquid segments are inserted into the first channel 12.

In addition, the insertion rate may be synchronized with a positioning rate at which the MFP head 10 is changed position above target areas of the surface 2, to ensure a correct separation of the liquid volumes 22, 24. Thus, information provided by the detection unit is optional, albeit useful for synchronizing purposes.

The insertion rate provided may for instance translate as a number of spacers inserted during a given time interval T, while the positioning rate is defined as a number of target areas 2a-2c processed by the head 10 during the same time interval T. Then, a synchronization of the insertion rate with the positioning rate can be simply achieved by setting the insertion rate equal to the positioning rate. Still, the insertion rate can be refined thanks to inputs provided from the detection units, as described earlier.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

What is claimed is:

1. A method for characterizing responses of a ligand-functionalized surface, the method comprising:
    dispensing a segmented liquid flow comprising liquid sequences, each liquid sequence comprising:
        an analyte segment comprising biomolecules of analyte;
        a liquid spacer segment; and
        a wash segment comprising a washing liquid,
        whereby liquid spacer segments separate wash segments from analyte segments in the dispensed segmented liquid flow,
    performing a measurement cycle for each liquid sequence of said liquid sequences of the segmented liquid flow being dispensed, said measurement cycle comprising:
        ejecting the analyte segment, from said each liquid sequence as the segmented liquid flow is being dispensed, toward the ligand-functionalized surface for the ejected analyte segment to interact with ligands on the ligand-functionalized surface;
        extracting, from said each liquid sequence as the segmented liquid flow is being dispensed, the liquid spacer segment succeeding the analyte segment as the latter is being ejected; and
        ejecting the wash segment succeeding the extracted liquid spacer segment, from said each liquid sequence as the segmented liquid flow is being dispensed, for the ejected wash segment to flush unbound and/or weakly bound biomolecules of analytes from the ligand-functionalized surface; and
    reading out a signal of bound biomolecules of analytes on the ligand-functionalized surface, to characterize a response of the ligand-functionalized surface.

2. The method of claim 1, wherein reading out the signal is performed so as to characterize a biomolecular kinetic response of the ligand-functionalized surface.

3. The method of claim 2, further comprising obtaining, after a plurality of measurement cycles, a kinetic profile of the ligand-functionalized surface according to at least one of signals read out at said plurality of measurement cycles and interaction times of analyte segments ejected on the ligand-functionalized surface at said plurality of measurement cycles.

4. The method of claim 1, wherein:
    the ligand-functionalized surface is a surface of a layer that is permissive to light;
    said analyte segment and wash segment are ejected toward the surface on one side of this layer; and
    said signal is, at each measurement cycle, read out from another side of said layer, opposite to said one side.

5. The method of claim 1, wherein, at each measurement cycle, the signal is read out while flushing unbound and/or weakly bound biomolecules of analytes from the ligand-functionalized surface with the ejected wash segment.

6. The method of claim 1, wherein the analyte segment of one or more of the liquid sequences of the dispensed segmented liquid comprises labelled biomolecules of analyte.

7. The method of claim 6, wherein:
    the liquid sequences of the dispensed liquid flow comprise, each, analyte segments with distinct types of labelled biomolecules of analyte; and
    the ligand-functionalized surface comprises distinct types of receptors or multivalent receptors, with which distinct types of labelled biomolecules of analyte may interact, and wherein reading out comprises reading out signals of distinct types of bound, labelled biomolecules of analytes on the surface, to characterize the response thereof.

8. The method of claim 6, wherein the ligand-functionalized surface comprises immobilized thereon at least one of cells and nuclei patterned thereon.

9. The method of claim 8, wherein:
    the ligand-functionalized surface comprises cells patterned thereon; and
    the analyte segment of one or more of the liquid sequences of the dispensed segmented liquid comprises a probe solution, so as for ejected probes of the probe solution to interact with said cells on the ligand-functionalized surface and hybridize the latter.

10. The method of claim 9, wherein reading out the signal is performed so as to characterize a biomolecular kinetic response of hybridized cells on the ligand-functionalized surface.

11. The method of claim 1, wherein one or more of the liquid sequences comprise, each:
    a plurality of successive wash segments, each comprising a washing liquid; and
    a plurality of liquid spacer segments, each comprising oil, so as to separate the successive wash segments from each other and from the analyte segment in each of the one or more of the liquid sequences; and wherein measurement cycles performed for each of said one or more of the liquid sequences comprise, each:
  extracting, from said each liquid sequence, the plurality of liquid spacer segments, before, while or after the analyte segment is being ejected; and
  ejecting the plurality of wash segments for the latter to flush unbound and/or weakly bound biomolecules of analytes from the ligand-functionalized surface.

12. The method of claim 1, wherein the steps of ejecting the analyte segment, extracting the liquid spacer segment and ejecting the wash segment are performed using a microfluidic probe head brought into a position opposite the ligand-functionalized surface.

13. The method of claim 12, wherein the method further comprises scanning the microfluidic probe head over the ligand-functionalized surface to eject analyte segments of distinct ones of the liquid sequences toward the ligand-functionalized surface, at distinct locations thereof, for the ejected analyte segment to interact with ligands on the ligand-functionalized surface at said distinct locations.

14. The method of claim 12, wherein the microfluidic probe head comprises:
  an ejection channel leading to an ejection aperture on a processing surface of the microfluidic probe head; and
  an oil extraction channel joining the ejection channel at a junction that comprises a capillary array, the latter comprises hydrophobic capillary structures;
  wherein the method further comprises bringing said processing surface into a position opposite the ligand-functionalized surface, the segmented liquid flow being dispensed via the ejection channel, and wherein, at each measurement cycle performed, said liquid spacer segment is extracted via the oil extraction channel, the latter subject to a lower pressure than a capillary pressure caused by said capillary array, whereby liquid spacer segments are filtered through the hydrophobic capillary structures in the capillary array, while analyte segments and wash segments are maintained in the ejection channel and ejected via said ejection aperture.

15. The method of claim 14, wherein the microfluidic probe head further comprises an aspiration channel leading to an aspiration aperture on said processing surface, and the ligand-functionalized surface is immersed in an immersion liquid, the method further comprising:
  aspirating liquid including some of the immersion liquid via said aspiration aperture, into said aspiration channel, while dispensing the segmented liquid flow.

16. The method of claim 1, wherein the method comprises dispensing two or more of said liquid sequences at distinct locations on the ligand-functionalized surface and performing distinct measurement cycles at said distinct locations.

* * * * *